United States Patent [19]

Astles et al.

[11] Patent Number: 5,071,468

[45] Date of Patent: Dec. 10, 1991

[54] TRIAZOLOPYRIMIDINE HERBICIDES

[75] Inventors: David P. Astles; John E. Spencer; Andrew Flood, all of Sittingbourne, England

[73] Assignee: Shell Internationale Research Maatschappij B.V., Netherlands

[21] Appl. No.: 446,142

[22] Filed: Dec. 5, 1989

[30] Foreign Application Priority Data

Dec. 23, 1988 [GB] United Kingdom ............... 8830182

[51] Int. Cl.$^5$ ............................................ A01N 43/90
[52] U.S. Cl. ..................................... 71/92; 544/263
[58] Field of Search ........................... 544/263; 71/92

[56] References Cited

U.S. PATENT DOCUMENTS

| | | | |
|---|---|---|---|
| 4,622,063 | 11/1986 | Nagano et al. | 71/92 |
| 4,650,892 | 3/1987 | Kleschick et al. | 544/263 |
| 4,668,278 | 5/1987 | Haga et al. | 71/92 |
| 4,734,123 | 3/1988 | Monte | 544/263 |
| 4,752,325 | 6/1988 | Haga et al. | 71/92 |
| 4,755,212 | 7/1988 | Kleschick et al. | 544/263 |
| 4,854,964 | 8/1989 | Jelich et al. | 544/263 |
| 4,910,306 | 3/1990 | McKendry | 544/263 |
| 4,960,455 | 10/1990 | Jelich et al. | 544/263 |
| 4,979,981 | 12/1990 | Pearson et al. | 71/92 |

FOREIGN PATENT DOCUMENTS

| | | | |
|---|---|---|---|
| 142152 | 5/1985 | European Pat. Off. | |
| 142811 | 5/1985 | European Pat. Off. | |
| 0375076 | 6/1990 | European Pat. Off. | 544/263 |
| 951652 | 3/1964 | United Kingdom | |

Primary Examiner—Donald G. Daus

[57] ABSTRACT

Compounds of the formula:

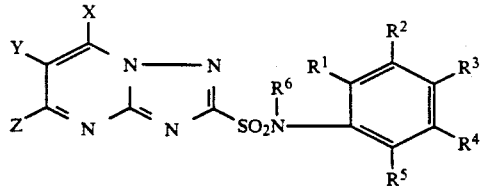

wherein
X, Y and Z are hydrogen, halogen, alkyl, haloalkyl, hydroxy, alkoxyalkyl, alkoxy, haloalkoxy, cycloalkyl, substituted aryl, alkylthio, arylthio, substituted amino or $-CO_2R^7$, wherein $R^7$ is hydrogen, optionally substituted alkyl, cycloalkyl, aryl or aralkyl, or X and Y together or Y and Z together form a ring $R^1$ is
$-A-CH=CHCH_3$, $\quad -A-C\equiv CCH_3$,
$-A-CH_2CH=CH_2$, $\quad -A-CH_2C\equiv CH$,
$-A(CH_2)_nBr$, $-A(CH_2)_nB(CH_2)_mBR$,

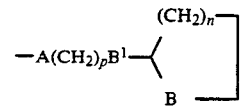

or $-A(CH_2)_nR^8$, optionally substituted wherein
A and B are $-O-$, $-S-$ or $-NR$, $B^1$ is a direct bond, $-O-$, $-S-$ or $-NR$, n and m are integers from 1 to 3, p is 0, 1 or 2, R is hydrogen, optionally substituted alkyl, cycloalkyl, aryl or aralkyl and $R^8$ is optionally substituted aryl;
$R^2$ to $R^4$, each are hydrogen, halogen, alkyl, alkoxy or $-CO_2R^7$;
$R^5$ is hydrogen, halogen, alkyl, haloalkyl, optionally substituted cycloalkyl or aryl, nitro, cyano, hydroxy, optionally substituted alkoxy, aryloxy, heteroaryloxy, amino, alkylthio, alkylsulphinyl, alkylsulfphonyl, arylthio, arylsulphinyl, or arylsulphonyl, oximino, oxime, oxime ether, $-CO_2R^7$, $-CONR_2^7$, $-SO_3R^7$, $-SO_2NR_2^7$, optionally substituted acyl, or arylcarbonyl

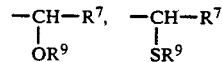

or the same as R, and $R^9$ is hydrogen, alkyl, acyl, arylcarbonyl or aralkyl; and
$R^6$ is hydrogen, acyl, arylcarbonyl, alkylsulphonyl, arylsulphonyl or alkyl, or salts are used in combating undesired plant growth.

7 Claims, No Drawings

TRIAZOLOPYRIMIDINE HERBICIDES

The present invention is concerned with certain heterocyclic compounds which have been found to have herbicidal activity. In particular the invention is concerned with novel triazolopyrimidine sulphonamides which are herbicidally active and can be used to provide for broad-leaved weed control with cereal selectivity.

EP-A-142152 discloses certain triazolopyrimidine sulphonamides having herbicidal activity, including compounds of the general formula:

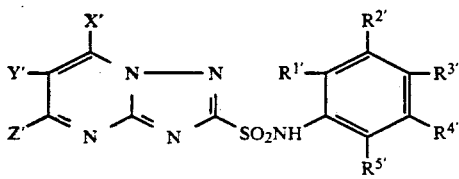

wherein X', Y' and Z' independently represent hydroxy, carboxyl, hydrogen, alkyl, haloalkyl, alkoxy, haloalkoxy, aryl, substituted aryl, alkylthio, halogen, amino, or two adjacent substituents are joined together in a cyclic structure; and $R^{1'}$, $R^{2'}$, $R^{3'}$, $R^{4'}$ and $R^{5'}$ independently represent hydrogen, halogen, alkyl, haloalkyl, aryl, substituted aryl, hydroxy, alkoxy, haloalkoxy, aryloxy, substituted aryloxy, heteroaryloxy, substituted heteroaryloxy, amino, alkylamino, dialkylamino, nitro, alkylthio, haloalkylthio, alkylsulphinyl, haloalkylsulphinyl, alkylsulphonyl, haloalkylsulphonyl, substituted or unsubstituted arylthio, substituted or unsubstituted arylsulphinyl, substituted or unsubstituted arylsulphonyl, cyano, carboxylic acids (and derivatives of carboxylic acids such as esters derived from readily available alcohols and amides derived from ammonia or readily available primary or secondary amines), sulphonic acids (and derivatives of sulphonic acids such as sulphonates derived from readily available alcohols and sulphonamides derived from ammonia or readily available primary or secondary amines); formyl, alkylcarbonyl, haloalkylcarbonyl, arylcarbonyl, substituted arylcarbonyl, oximino, oxime ethers, carbinol (and carbinol derivatives such as ethers and esters derived from readily available alkylating agents and carboxylic acids respectively) and mercaptoalkyl (and derivatives of mercaptoalkyl groups such as thioethers and thioesters derived from readily available alkylating agents and carboxylic acids respectively).

We have now found that triazolopyrimidine sulphonamides in which the sulphonamido nitrogen atom is substituted by certain ortho-substituted benzene groups have valuable herbicidal activity. We have found that such triazolopyrimidine sulphonamides give control of a range of broad-leaved weeds with cereal selectivity.

Accordingly, the present invention provides a triazolopyrimidine sulphonamide derivative of the general formula (I)

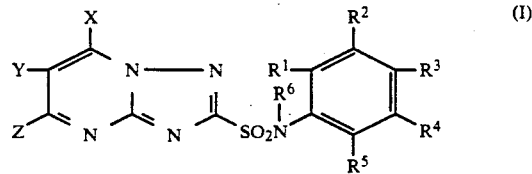

wherein

X, Y and Z which may be the same or different, each represents hydrogen, halogen, alkyl, haloalkyl, hydroxy, alkoxyalkyl, alkoxy, haloalkoxy, cycloalkyl, optionally substituted aryl, alkylthio, arylthio, optionally substituted amino or a group $-CO_2R^7$, wherein $R^7$ is hydrogen, optionally substituted alkyl, optionally substituted cycloalkyl, optionally substituted aryl or optionally substituted aralkyl, or X and Y together or Y and Z together represent a divalent group forming, together with the carbon atoms to which they are attached, a ring structure;

$R^1$ represents a group $-A-C\equiv CCH_3$, $-A-CH_2CH=CH_2$, $-ACH=CHCH_3$, $-ACH_2C\equiv CH$, $-A(CH_2)_nBR$, $-A(CH_2)_nB(CH_2)_mBR$,

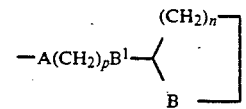

$-A(CH_2)_nR^8$, wherein optionally substituted at any chain or ring carbon atom, wherein A and B independently represent $-O-$, $-S-$ or $-NR$, $B^1$ represents a direct bond, $-O-$, $-S-$ or $-NR$, n and m are integers from 1 to 3, p is 0, 1 or 2, R is hydrogen, optionally substituted alkyl, optionally substituted cycloalkyl, optionally substituted aryl or optionally substituted aralkyl and $R^8$ is optionally substituted aryl;

$R^2$ to $R^4$, which may be the same or different, each represents hydrogen, halogen, alkyl, alkoxy or $-CO_2R^7$, wherein $R^7$ is as herein defined; $R^5$ is hydrogen, halogen, alkyl, haloalkyl, optionally substituted cycloalkyl optionally substituted aryl, nitro, cyano, hydroxy, optionally substituted alkoxy, optionally substituted aryloxy, optionally substituted heteroaryloxy, optionally substituted amino, optionally substituted alkylthio, optionally substituted alkylsulphinyl, optionally substituted alkylsulphonyl, optionally substituted arylthio, optionally substituted arylsulphinyl, optionally substituted arylsulphonyl, oximino, oxime, oxime ether $-CO_2R^7$, $-CONR^7_2$, $-SO_3R^7$, $-SO_2NR^7_2$, optionally substituted acyl, optionally substituted arylcarbonyl,

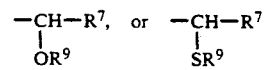

or has the same meaning as R, wherein $R^7$ is as herein defined and $R^9$ is hydrogen, alkyl, acyl, arylcarbonyl or aralkyl; and $R^6$ is hydrogen, acyl, arylcarbonyl, alkylsulphonyl, arylsulphonyl or alkyl, subject to the proviso that $R^1$ does not represent $-SCH_2CH=CH_2$ when Y and $R^2$ to $R^5$ are hydrogen and X and Z are methyl.

Preferably Y is hydrogen and X and Z, which may be the same or different, are alkyl, especially $C_1$-$C_4$ alkyl. The ortho substituent $R^1$ preferably is —OCH$_2$CH=CH$_2$, —OCH$_2$C≡CH, —A(CH$_2$)$_n$BR, —A(CH$_2$)$_n$B(CH$_2$)$_m$BR,

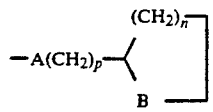

or —A(CH$_2$)$_n$R$^8$ wherein R is hydrogen, $C_1$-$C_4$alkyl or aryl (preferably phenyl).

The most preferred compounds of formula (I) are those wherein Y is hydrogen, X and Z are both methyl, $R^2$ to $R^4$ are hydrogen, $R^1$ is —OCH$_2$CH=CH$_2$, —OCH$_2$C≡CH, —A(CH$_2$)$_n$BR$^{10}$, —O(CH$_2$)$_n$O(CH$_2$)OR$^{10}$,

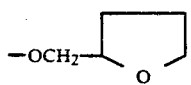

or —OCH$_2$C$_6$H$_5$, wherein A, B, n and m are as defined herein and R$^{10}$ is hydrogen or $C_1$-$C_4$ alkyl, R$^5$ is hydrogen, fluorine, chlorine, nitro, $C_1$-$C_4$alkoxy or —A(CH$_2$)$_n$BR$^{10}$ and R$^6$ is hydrogen, acyl of up to 4 carbon atoms, $C_1$-$C_4$alkyl or the group:

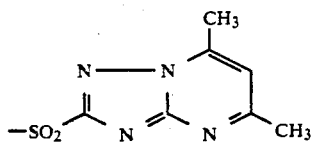

Unless otherwise specified in this specification, an alkyl group may be linear or branched and may contain up to 10, preferably up to 6, carbon atoms, suitable examples being methyl, ethyl and propyl. A cycloalkyl group suitably has from 3 to 7 ring carbon atoms. Furthermore, an aryl group may contain up to 10 ring atoms and may be a carbocyclic aromatic system or heterocyclic aromatic system. An aryl group may comprise a single ring or a fused ring system and may have from 0 to 3 hetero ring atoms. Suitable examples of an aryl group include phenyl, pyridyl, furyl, thienyl, pyrimidinyl and triazolyl.

When any groups are designated as being optionally substituted, the substituent groups which are optionally present may be any of those customarily employed in the development of pesticidal compounds, and/or the modification of such compounds to influence their structure/activity, persistence, penetration or other property. In relation to alkyl, alkenyl and alkynyl groups, specific examples of such substitutents include halogen, especially fluorine, chlorine or bromine atoms, and nitro, cyano, hydroxyl, $C_{1-4}$ alkyl, $C_{1-4}$ haloalkyl, $C_{1-4}$ alkoxy, $C_{1-4}$ haloalkoxy and ($C_{1-4}$ alkoxy)carbonyl groups and amino and oximino groups themselves optionally substituted by 1 or 2 $C_{1-4}$ alkyl groups. It is preferred, however, that alkyl, alkenyl and alkynyl moieties in compounds of formula I are unsubstituted. In relation to an aryl moiety, optional substituents include halogen, especially fluorine, chlorine and bromine atoms, and nitro, cyano, amino, hydroxyl, $C_{1-4}$ alkyl, $C_{1-4}$ haloalkyl (especially CF$_3$) and $C_{1-4}$ alkoxy groups. 1 to 3 substituents may suitably be employed. In the case of optionally substituted amino or oximino groups, substituents are preferably selected from $C_{1-4}$ alkyl, phenyl and amino groups.

It is to be understood that where it is possible for a compound of the formula (I) to exist in more than one stereoisomeric form then the present invention extends to all such isomers.

The present invention extends to salts of the compounds of general formula (I), preferably agriculturally suitable salts. Salt formation may occur at, for example, any free amino group. Examples of such salts are acid addition salts with inorganic or organic acids, e.g. sodium salts, and ammonium salts.

The compounds of general formula (I) are suitably prepared by the reaction of a substituted aniline with a 1,2,4-triazolo[1,5-a]pyrimidine-2-sulphonyl halide as illustrated by the following reaction scheme;

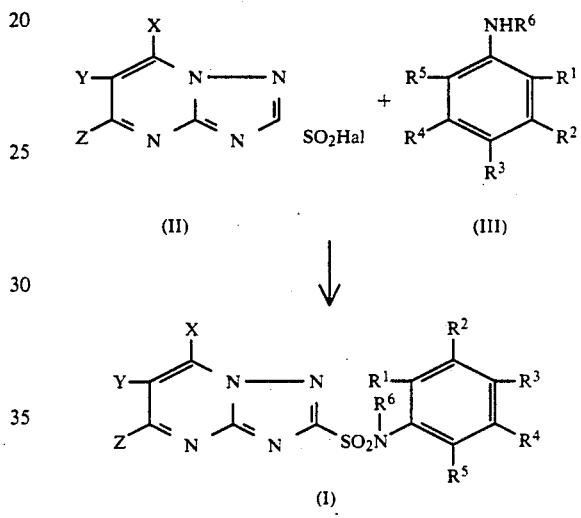

wherein Hal denotes a halogen atom, especially chlorine, R$^6$ is hydrogen or alkyl, and the other symbols are as previously defined herein; and, if desired or required, converting a compound of the general formula (I) into another compound of the general formula (I), for example into a compound (I) in which R$^6$ is other than hydrogen or alkyl.

The reactant of general formula (III) may be used in the form of the free aniline compound or in the form of a reactive derivative, for example a salt.

During the reaction it will, of course, be understood that any free reactive groups present as a substituent X, Y, Z, R$^1$, R$^2$, R$^3$, R$^4$, R$^5$ or R$^6$ are suitably protected, and the protecting group removed following the reaction.

The reaction is preferably carried out in the presence of a base, which may be an organic or inorganic base. As an organic base, an aliphatic or aromatic amine, for example pyridine, especially dry pyridine, is most suitable. As an inorganic base, sodium hydride may especially be mentioned. The base may act as the solvent for the reaction, or, in addition to the base, a suitable inert organic solvent of mixture of solvents may be used.

Preferably the reaction is carried out in the absence of water. Suitably the materials employed in the reaction are dried prior to use.

The reaction may be carried out at a temperature in the range of from 0° C. to reflux, but preferably is carried out at ambient temperature. The reactants are suitably used in a 1:1 molar ratio, but an excess of either reactant may be employed.

Suitably the reaction is carried out in accordance with the methods described in EP-A-142152.

The reaction may be followed by any of the customary isolation/separation and/or purification techniques, such as chromatography and/or recrystallisation procedures.

It is, of course, possible to convert one compound of the general formula (I) into another compound of the general formula (I) by conventional techniques, and the present invention is to be understood to encompass such a mode of preparation of compounds of the invention. For example, a compound of the general formula (I) in which $R^6$ is other than hydrogen may be prepared from a compound of the general formula (I) in which $R^6$ is hydrogen. Thus, acyl $R^6$ may be prepared by refluxing a compound of the general formula (I) in which $R^6$ is hydrogen with acetic anhydride, and methyl $R^6$ may be prepared by reacting the corresponding N-unsubstituted compound with sodium hydride under suitable reaction conditions, for example in dry tetrahydrofuran under a nitrogen blanket and followed by the addition of iodomethane.

Compounds of the general formula (II) are known and may be prepared using methods known from literature, for example as described in EP-A-142811, by reaction of a corresponding mercapto, or arylmethylthio, compound with a hypochlorite solution in a two phase solvent system comprising an aqueous acidic phase and a water-immiscible organic phase.

The compounds of the general formula (III) may be prepared, using a variety of techniques described in literature, from the corresponding nitro compounds by, for example, reduction using hydrated stannous chloride ($SnCl_2.2H_2O$) in refluxing ethanol, or with hydrogen in the presence of a catalyst, preferably platinum metal or oxide. The nitro compounds themselves may be prepared by conventional techniques, and may, for example, be prepared by reacting a nitrophenol which has the substituents $R^2$, $R^3$, $R^4$ and $R^5$ on the phenyl ring, with a compound of the general formula $R^1A$ in which $R^1$ is as previously defined herein and A is a leaving group (i.e. a group that will cleave from the starting material under the reaction conditions thus promoting reaction at a specified site), preferably a bromine atom, in basic conditions, for example, in the presence of dry acetone and potassium carbonate, or, more especially, in the presence of a phase-transfer catalyst, such as triethylbenzylammonium chloride, and sodium hydroxide.

The nitrophenol starting materials may be prepared in accordance with known techniques, such as are described by Hodgson, H.H., and Moore, F.H., J.Chem. Soc. (1925), 1599; Hodgson, H.H., and Nixon, J.,J.Chem. Soc. (1928) 1979; or Wright, J., et al, J. Med. Chem. (1979), 22(2), 210.

The compounds of the general formula (I) have been found to possess useful herbicidal properties, and accordingly the invention provides a herbicidal composition containing such a compound. Further, in accordance with the invention, there is provided a method of preventing or combating undesired plant growth at a locus by treating the locus with a compound of formula (I) or composition containing such a compound. Application to the locus may be pre-emergence or post-emergence. The dosage of active ingredient used may, for example, be in the range from 0.01 to 10kg/ha, preferably from 0.05 to 4kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example compounds possessing herbicidal, insecticidal or fungicidal properties.

The following Examples illustrate the invention.

Table I, which follows, summarises the structure and physical properties of prepared compounds of the invention in which each of X and Z represents methyl, each of Y, $R^2$, $R^3$ and $R^4$ represents hydrogen, and $R^1$, $R^5$ and $R^6$ have the meanings given.

The mode of preparation of the compounds of Table I is described in Preparation Examples I to 6. The structure of each compound prepared was confirmed by NMR and mass spectra.

TABLE I

| Compound No. | $R^6$ | $R^5$ | $R^1$ | M. Pt (°C.) | Calc. C | Calc. H | Calc. N | Found C | Found H | Found N |
|---|---|---|---|---|---|---|---|---|---|---|
| 1 | H | Cl | O-allyl | 157 | 48.8 | 4.1 | 17.8 | 48.0 | 3.8 | 17.1 |
| 2 | H | Cl | O-allyl | 218 | 49.0 | 3.6 | 17.9 | 48.8 | 4.2 | 17.2 |
| 3 | H | Cl | OCH₂CH₂OEt | 154 | 49.7 | 5.1 | 17.1 | 48.6 | 4.8 | 16.7 |
| 4 | H | Cl | OCH₂-Ph | oil | 54.1 | 4.1 | 15.8 | 54.4 | 4.2 | 15.8 |
| 5 | H | F | O-allyl | 155 | 50.9 | 4.2 | 18.6 | 48.6 | 4.2 | 18.4 |
| 6 | H | Cl | OCH₂OMe | 152 | 45.3 | 4.0 | 17.6 | 45.0 | 4.0 | 16.8 |
| 7 | H | Cl | OCH₂CH₂OH | oil | 45.3 | 4.0 | 17.6 | 47.6 | 4.0 | 16.5 |
| 8 | H | Cl | OCH₂CH₂OMe | 177 | 46.7 | 4.4 | 17.0 | 46.0 | 4.1 | 16.8 |
| 9 | H | F | OCH₂CH₂OEt | oil | 49.9 | 4.9 | 17.1 | 50.0 | 5.1 | 16.7 |
| 10 | H | Cl | OCH₂CH₂OPr$^n$ | oil | 49.0 | 5.2 | 15.9 | 48.5 | 4.8 | 15.6 |
| 11 | H | F | OCH₂CH₂OMe | 86 | 48.6 | 4.6 | 17.7 | 48.0 | 4.8 | 17.1 |
| 12 | H | F | OCH₂CH₂OPr$^n$ | 106.3 | 51.1 | 5.2 | 16.5 | 50.5 | 5.1 | 15.9 |
| 13 | H | F | OCH₂CH₂SMe | 59 | 46.7 | 4.4 | 17.0 | 42.9 | 4.3 | 14.9 |
| 14 | H | F | OCH₂CH₂NMe₂ | 265 | 50.0 | 5.1 | 20.6 | 49.6 | 5.1 | 18.2 |
| 15 | H | Cl | OCH₂CH₂OMe | oil | 47.8 | 4.9 | 16.4 | 43.0 | 4.6 | 13.6 |
| 16 | H | H | OCH₂CH₂OEt | oil | 52.2 | 5.4 | 17.9 | 49.7 | 5.7 | 16.2 |
| 17 | H | H | NHCH₂CH₂OMe | 157 | 51.1 | 5.3 | 22.3 | 49.3 | 5.3 | 21.5 |
| 18 | H | OCH₂CH₂OEt | OCH₂CH₂OEt | oil | 52.6 | 6.1 | 14.6 | 51.4 | 6.1 | 14.0 |
| 19 | H | OMe | OCH₂CH₂OEt | oil | 51.3 | 5.5 | 16.6 | 51.4 | 6.3 | 16.6 |
| 20 | H | H | SCH₂CH₂OMe | oil | 48.9 | 4.8 | 17.8 | — | — | — |
| 21 | H | Cl | OCH₂CH₂OPr$^i$ | 93 | 49.0 | 5.2 | 15.9 | 46.4 | 4.8 | 15.6 |

TABLE I-continued

[Structure: 5,7-dimethyl-1,2,4-triazolo[1,5-a]pyrimidine-2-sulfonamide core with substituted phenyl bearing R¹, R², R³, R⁴, R⁵ and N-R⁶]

| Compound No. | R⁶ | R⁵ | R¹ | M. Pt (°C.) | Calc. C | Calc. H | Calc. N | Found C | Found H | Found N |
|---|---|---|---|---|---|---|---|---|---|---|
| 22 | H | Cl | OCH₂CH₂O—(phenyl) | 175 | 53.2 | 4.2 | 14.8 | 52.5 | 4.4 | 15.3 |
| 23 | H | Cl | OCH₂—(tetrahydrofuran) | 96 | 49.4 | 4.6 | 16.0 | 45.7 | 4.3 | 15.0 |
| 24 | —C(=O)—CH₃ | Cl | OCH₂CH₂OEt | 132 | 48.8 | 4.7 | 15.0 | 49.0 | 4.8 | 14.6 |
| 25 | —C(=O)—CH₃ | Cl | OCH₂CH₂OMe | 155 | 47.5 | 4.6 | 15.4 | 48.2 | 4.6 | 15.0 |
| 26 | Me | Cl | OCH₂CH₂OEt | oil | 49.1 | 5.0 | 15.9 | 48.5 | 5.0 | 15.1 |
| 27 | H | NO₂ | OCH₂CH₂OEt | 190.0 | 46.8 | 4.6 | 19.3 | 45.8 | 4.5 | 18.8 |
| 28 | H | F | OCH₂OCH₂CH₂OMe | 149.0 | 48.0 | 4.7 | 16.5 | 47.3 | 4.9 | 15.9 |
| 29 | [pyrimidine-CH₃ ring structure with SO₂] | Cl | OCH₂CH₂OEt | 290.0 | 44.6 | 4.0 | 21.7 | 44.3 | 4.1 | 21.8 |

PREPARATION OF EXAMPLE 1

Variant A a) 4.7g of 3-chloro-2-nitrophenol in 30ml of acetone were treated with 3.7g potassium carbonate and then reacted with 3.25g allylbromide under reflux for 8 hours. The reaction mixture was cooled and filtered and the residue extracted into chloroform, washed once with water, dried using sodium sulphate and 6.5g of an oily residue obtained The crude product was then purified by flash chromatography to give 4.85g of 3-chloro-2-nitrophenyl allyl ether as a colourless oil (yield 84%).

b) 1g of the oil prepared in a) was dissolved in 10ml of ethanol and treated with 5.28g of hydrated stannous chloride (SnCl₂.2H₂O) at 70° C. for 90 minutes. The reaction mixture was cooled and quenched with 50g of ice. A white solid was produced which was then dispersed in 10 ml of water, and solid sodium bicarbonate added to adjust the pH to a pH of 7. The mixture was filtered and the residue washed thoroughly three times with 50ml aliquots of ethyl acetate and the filtrate extracted also with ethyl acetate. The extracts were combined, washed with water, dried over sodium sulphate and evaporated to give 0.74g (86% yield) of 2-amino-3-chlorophenyl allyl ether.

c) 0.77g of 2-amino-3-chlorophenyl allyl ether in 12ml of dry pyridine were treated with 1.03g of 5,7-dimethyl-1,2,4-triazolo[1,5-a]pyrimidine-2-sulphonyl chloride and stirred at ambient temperature overnight. The pyridine was removed by evaporation with final traces eliminated by means of a vacuum pump. An oily brown product was obtained which was stirred with 30ml of 1M sodium hydroxide for 20 minutes to give a brown solution. Charcoal (20–30mg) was added and the mixture stirred for 10 minutes and then filtered through Celite ("Celite" is a trade mark). The filtrate was cooled, acidified with 10% hydrochloric acid to pH 1-2 to produce a solid which was then filtered off, washed with water and dried in vacuo to give 1.2g (a yield of 73%) of 5,7-dimethyl-2-(N-[2-allyloxy-6-chlorophenyl]-sulphamoyl)-1,2,4-triazolo[1,5-a]pyrimidine (Compound No. 1).

Variant B a) 1.82g of 3-fluoro-2-nitrophenyl (2-dimethylaminoethyl) ether were prepared in analogous manner to that described in a) above from 2g of 3-fluoro-2-nitrophenol using potassium carbonate and 2-dimethylaminoethyl chloride generated from the more stable hydrochloride salt.

b) 1.44g of the ether of a), a brown oil, were dissolved in 50ml of ethanol and the mixture subjected to hydrogenation in the presence of 0.15g of platinum oxide (PtO₂) as catalyst at a pressure of 40psi (276KPa) over 1 hour at 20° C. The catalyst was filtered off on Hyflo ("Hyflo" is a trademark) and the solvent evaporated off to give 1.21g of 2-(2-dimethylaminoethoxy)-6-fluoroaniline as an oil.

c) 1.1g of the aniline was then reacted with 1.37g of 5,7-dimethyl-1,2,4-triazolo[1,5-a]pyrimidine-2-sulphonyl chloride in 50ml of dry pyridine in analogous manner to that described in Variant A c) above to give 0.88g (39% yield) of 5,7-dimethyl-2-(N-[2-(2-dimethylaminoethoxy)-6-fluoro-phenyl]-sulphamoyl-1,2,4-triazolo[1,5-a]-pyrimidine (Compound No. 14).

In analogous manner to Preparation Example 1, the following compounds were prepared from the appropriate starting materials:

Variant A 5,7-dimethyl-2-(N-[2-chloro-6-propargyloxyphenyl]-sulphamoyl)-1,2,4-triazolo[1,5-a]pyrimidine (Compound No. 2)- using acetonitrile as the solvent in process a) instead of acetone;

5,7-dimethyl-2-(N-[2-chloro-6-(2-ethoxyethoxy)-phenyl]-sulphamoyl)-1,2,4-triazolo[1,5-a]pyrimidine (Compound No. 3);

5,7-dimethyl-2-(N-[2-benzyloxy-6-chlorophenyl]-sulphamoyl)-1,2,4-triazolo[1,5-a]pyrimidine (Compound No. 4);

5,7-dimethyl-2-(N-[2-allyloxy-6-fluorophenyl]-sulphamoyl)-1,2,4-triazolo[1,5-a]pyrimidine (Compound No. 5);

5,7-dimethyl-2-(N-[2-chloro-6-(2-methoxymethoxy)-phenyl]-sulphamoyl)-1,2,4-triazolo[1,5-a]pyrimidine (Compound No. 6);

5,7-dimethyl-2-(N-[2-chloro-6-(2-hydroxyethoxy)-phenyl]-sulphamoyl)-1,2,4-triazolo[1,5-a]pyrimidine (Compound No. 7):

5,7-dimethyl-2-(N-[2-2-ethoxyethoxy)-6-fluorophenyl]-sulphamoyl)-1,2,4-triazolo[1,5-a]pyrimidine (Compound No. 9):

5,7-dimethyl-2-(N-[2-fluoro-6-(2-methylthioethoxy)-phenyl]-sulphamoyl)-1,2,4-triazolo[1, 5-a]pyrimidine (Compound No. 13).

Variant B 5,7-dimethyl-2-(N-[2-chloro-6-(2-phenoxyethoxy)-phenyl]sulphamoyl)-1,2,4-triazolo[1,5-a]pyrimidine (Compound No. 22)

PREPARATION EXAMPLE 2

In analogous manner to that described in Preparation Example 1 Variant A a), 3g of 2-[3-fluoro-2-nitrophenoxy]ethanol were prepared from 5g of 3-fluoro-2-nitrophenol. 1.4g of the alcohol were then reacted with 7ml methyliodide with the addition of 14ml of 50% sodium hydroxide and 0.1g of the phase transfer catalyst, triethylbenzylammonium chloride. The mixture was stirred at room temperature for 2 hours. 20ml of water was then added and the product extracted into 50ml diethyl ether and the ether layer dried using magnesium sulphate. 0.8g (yield of 53%) of 3-fluoro-2-nitrophenyl (2-methoxyethyl) ether were obtained, after the solvent had been removed by evaporation, as an oil which solidified on standing. 0.8g (54% yield) of 5,7-dimethyl-2-(N-[2-fluoro-6-(2-methoxyethoxy)-phenyl]-sulphamoyl)-1,2,4-triazolo[1,5-a]pyrimidine (Compound No. 11) were prepared from the ether via the 2-amino derivative in an analogous procedure to that described in Preparation Example 1, Variant A.

By an analogous procedure the following compounds were prepared from the appropriate starting materials:

5,7-dimethyl-2-(N-[2-chloro-6-(2-methoxyethoxy)-phenyl]-sulphamoyl-1,2,4-triazolo[1,5-a]pyrimidine (Compound No. 8);

5,7-dimethyl-2-(N-[2-chloro-6-(2-n-propoxyethoxy)-phenyl]-sulphamoyl)-1,2,4-triazolo[1,5-a]pyrimidine (Compound No. 10);

5,7-dimethyl-2-(N-[2-chloro-6-(3-methoxy-n-propoxy)-phenyl]-sulphamoyl)-1,2,4-triazolo[1,5-a]pyrimidine (Compound No. 15);

5,7-dimethyl-2-(N-[2-chloro-6-(2-isopropoxy)ethoxyphenyl]-sulphamoyl)-1,2,4-triazolo[1,5-a]pyrimidine (Compound No. 21);

and, using Preparation Example 1, Variant B, procedures instead of Preparation Example 1, Variant A, 5,7-dimethyl-(N-[2-fluoro-6-(2-n-propoxyethoxy)-phenyl]-sulphamoyl)-1,2,4-triazolo[1,5-a]pyrimidine (Compound No. 12).

PREPARATION EXAMPLE 3 a) To 30g of 2-ethoxyethanol in 300ml of tetrahydrofuran 27.4ml of pyridine were added and 26.4ml of mesyl chloride added dropwise at room temperature over 15 minutes. The mixture was refluxed overnight, the solid that formed filtered off and the solvent evaporated off from the residue. The residue was distilled under 20m Hg to give 2-ethoxyethyl methanesulphonate.

b) 2g of 2-nitrophenol were added to a solution of 0.57g of sodium hydroxide solution in 20ml of water and 10ml of methanol, the mixture stirred for 15 minutes at room temperature and the sulphonate product of a) added (2.66g). The reaction mixture was refluxed overnight and the product extracted into dichloromethane. Drying with sodium sulphate followed, the solvent evaporated off and the crude product purified by flash chromatography to give 1g of 2-nitrophenyl (2-ethoxyethyl) ether as a yellow oil.

c) 0.8g of the product of b) was then converted to the corresponding aniline (a brown oil) using 3.45g of hydrated stannous chloride in analogous procedure to that of Preparation Example 1, Variant A c) and thence by reaction with 0.74g of 5,7-dimethyl-1,2,4-triazolo[1,5-a]pyrimidine-2-sulphonyl chloride in 15ml dry pyridine to give 0.7g (44% yield) of 5,7-dimethyl-2-(N-[2-(2-ethoxyethoxy)phenyl]-sulphamoyl)-1,2,4-triazolo[1,5-a]pyrimidine (Compound 16) as an oil.

In analogous manner the following compounds were prepared from the appropriate starting materials:

5,7-dimethyl-2-(N-[2,6-di(2-ethoxyethoxy)phenyl]-sulphamoyl)-1,2,4-triazolo[1,5-a]pyrimidine (Compound No. 18);

5,7-dimethyl-2-(N-[2-2-ethoxyethoxy)-6-methoxyphenyl]-sulphamoyl)-1,2,4-triazolo[1,5-a]pyrimidine (Compound No. 19)- using methyl-p-toluene-sulphonate;

5,7-dimethyl-2-(N-[2-chloro-6-tetrahydrofurfur-2-yloxyphenyl]-sulphamoyl)-1,2,4-triazolo[1,5-a]pyrimidine (Compound No. 23).

PREPARATION EXAMPLE 4 a) To 28.2g of 2-fluoronitrobenzene in 70ml of n-butanol 30.0g of 2-methoxyethylamine were added and the mixture refluxed overnight to give a dark red solution. After cooling the n-butanol was evaporated off and the product extracted into diethyl ether. The diethyl ether was then washed twice with dilute (aqueous) hydrochloric acid, once with dilute (aqueous) sodium carbonate and once with brine. The ether was then dried using magnesium sulphate and evaporated off to give 35g of 2-(2-methoxyethylamino)nitrobenzene as a red liquid.

b) In analogous manner to that described in Preparation Example I, Variant A b) and c), the 2-(2-methoxyethylamino)nitrobenzene of a) above was converted into the corresponding aniline under the action of hydrated stannous chloride, and the resulting aniline was reacted with 0.8g of 5,7-dimethyl-1,2,4-triazolo[1,5-a]pyrimidine-2-sulphonyl chloride in 15ml dry pyridine to provide 5,7-dimethyl-2-(N-[2-(2-methoxyethylamino)-phenyl]-sulphamoyl)-1,2,4-triazolo[1,5-a]pyrimidine (Compound No. 17) -0.7g, a yield of 57%, as an oily solid.

In analogous manner the following compound was prepared from the appropriate starting materials: 5,7-dimethyl-2-(N-[2-(2-methoxyethylthio)phenyl]-sulphamoyl) -1,2,4-triazolo[1,5-a]pyrimidine (Compound No. 20)—using 2-mercaptoethanol, instead of 2-methoxyethylamine, and methylating the resulting nitrobenzene with methyl iodide in sodium hydroxide under the action of the phase transfer catalyst triethylbenzylammonium chloride to produce the methoxy analogue.

PREPARATION EXAMPLE 5

Variant A 1g of 5,7-dimethyl-(N-[2-chloro-6-(2-ethoxyethoxy)-phenyl]-sulphamoyl)-1,2,4-triazolo[1,5-a]pyrimidine (prepared using the procedures described, in Preparation Example 1, Variant A, was stirred in acetic anhydride at reflux overnight. The resulting clear solution was cooled and the acetic anhydride removed under reduced pressure. The oil prepared was dissolved in ethyl acetate (50ml), the solution was washed with saturated NaHCO$_3$ (2×50ml), water (50ml), dried (MgSO$_4$), filtered and concentrated to yield the desired product as a straw-coloured oil which solidified on standing. 0.95g (a yield of 86.5%) of 5,7-dimethyl-2-(N-acetyl-N-[2-chloro-6-(2-ethoxyethoxy)phenyl]-sulphamoyl)-1,2,4-triazolo[1,5-a]pyrimidine (Compound No. 24) was prepared.

In analogous manner, the following compound was prepared from the appropriate starting materials: 5,7-dimethyl-2-(N-acetyl-N-[2-chloro-6-(2-methoxyethoxy)phenyl]-sulphamoyl)-1,2,4-triazolo[1,5-a]pyrimidine (Compound No. 25)

Variant B 1.5g of 5,7-dimethyl-2-(N-[2-chloro-6-(2-ethoxyethoxy)phenyl]-sulphamoyl)-1,2,4-triazolo[1,5-a]pyrimidine (prepared using the procedures described in Preparation Example 1, Variant A, were stirred in dry tetrahydrofuran under dry nitrogen at ambient temperature. To the pale yellow solution was added 60% sodium hydride and a white floccular solid formed over 60 minutes. The tetrahydrofuran was removed and the sodium salt resuspended in dry dimethyl formamide. 0.5g of methyl iodide was added and the mixture stirred under nitrogen overnight at ambient temperature. After concentration of the reaction mixture the residue was treated with water and extracted twice with 20ml of ethyl acetate. The organic phases were combined, dried over magnesium sulphate, filtered and concentrated. The crude product was then purified by flash chromatography to give 1.1g (71% yield) of 5,7-dimethyl-2-(N-methyl-N-[2-chloro-6-(2-ethoxyethoxy)phenyl]-sulphamoyl)-1,2,4-triazolo[1,5-a]pyrimidine (Compound No. 26) as a white solid.

PREPARATION EXAMPLE 6 a) 10g of 2-amino-3-nitrophenol was dissolved in 100ml of acetic anhydride. 1g of sodium acetate was added and the mixture refluxed for 4 hours. After cooling, the anhydride was evaporated off and the brown residue purified by recrystallisation in petroleum ether-ether to give 13.7g of a light brown solid identified by NMR as 2-diacetylamino-3-nitrophenol (melting point 85° C.).

b) 8.6g of the purified product of a) was suspended in 80 ml of water, cooled to 5° C. in an ice bath and 50ml of 4N sodium hydroxide added dropwise with vigorous stirring whilst the temperature was maintained at less than 10° C. After 30 minutes' stirring much of the solid had dissolved. The reaction mixture was filtered, the residue washed twice with 10ml of water and the aqueous filtrate cooled to 10° C. and acidified slowly with conc. hydrochloric acid to pH 1. Extraction with dichloromethane (twice) was carried out and the combined dichloromethane extracts dried over sodium sulphate and the solvent evaporated off to give 5.4g of a yellow solid: 2-acetylamino-3-nitrophenol.

c) 1g of 2-acetylamino-3-nitrophenol was mixed with an aqueous solution of sodium hydroxide (0.21g of NaOH in 5ml H$_2$O) with stirring. 5ml of ethanol was added to the deep red solution formed and then 0.64ml of 2-bromoethyl ethyl ether added and the reaction mixture stirred for 1 hour at room temperature and refluxed overnight. After cooling 5ml of 2M sodium hydroxide was added to the mixture to increase the pH to pH 12. Then extraction with 2×15ml of dichloromethane was carried out, the combined dichloromethane extracts dried over sodium sulphate, the solvent evaporated off and the product purified by recrystallisation from ethanol/hexane/dioxan to leave 1.0g of 2-acetyl-3-nitrophenyl (2-ethoxyethyl) ether as a fine yellow solid.

d) 2.8g of 2-acetyl-3-nitrophenyl (2-ethoxyethyl) ether was added, in portions, to 0.6g of sodium hydride—a 60% oil dispersion in 50ml tetrahydrofuran—at 0° C. After stirring for 30 minutes at 0° C. the mixture was warmed to room temperature. The orange solution was cooled to 0° C. and 2.54g of 5,7-dimethyl-1,2,4-triazolo[1,5-a]pyrimidine-2-sulphonyl chloride added in small portions. The reaction mixture was warmed and stirred overnight at room temperature. The solvent was then evaporated off and the residue treated with 20ml of 1M sodium hydroxide, washed with ethyl acetate which was then back extracted with 10ml of 1M sodium hydroxide, the two NaOH extracts combined, filtered and acidified to give an oily yellow precipitate. The crude product was purified using dichloromethane and then by flash chromatography. 0.8g (17% yield) of 5,7-dimethyl-2-(N-[2-(2-ethoxyethoxy)-6-nitrophenyl]sulphamoyl)-1,2,4-triazolo[1,5-a]pyrimidine (Compound No. 27) was obtained as a yellow solid.

Herbicidal Activity

To evaluate their herbicidal activity, compounds or formula (I) were tested using as a representative range of plants: maize, *Zea mays* (Mz); *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5kg or 1kg of active material per hectare in a volume equivalent to 600 litres per hectare in the soil spray and foliar spray tests, and at a dosage level equivalent to 10 kilograms of active material per hectare in a volume equivalent to approximately 3,000 litres per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching in the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table II below. The symbols "-" indicates that no result was obtained.

TABLE II

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | 8 | 7 | 8 | 8 | 8 | 9 | 9 | 8 | 5 | 7 | 4 | 7 | 7 | 7 | 8 | 9 | 7 | 8 | 7 | 9 | 7 | 8 | 7 | 8 | 8 |
| | | | | | | | | | 1 | 1 | 0 | 6 | 3 | 1 | 7 | 7 | 6 | 6 | 1 | 7 | 4 | 5 | 6 | 8 | 8 |
| 2 | 6 | 5 | 7 | 7 | 8 | 8 | 8 | 8 | 5 | 5 | 6 | 6 | 7 | 5 | 8 | 7 | 7 | 8 | 8 | 8 | 6 | 7 | 7 | 8 | 8 |
| | | | | | | | | | 1 | 4 | 2 | 6 | 4 | 3 | 6 | 6 | 7 | 3 | 5 | 6 | 2 | 0 | 6 | 6 | 7 |
| 3 | 8 | 8 | 8 | 8 | 8 | 9 | 8 | 8 | 5 | 8 | 8 | 8 | 7 | 8 | 9 | 9 | 8 | 8 | 8 | 8 | 8 | 8 | 7 | 8 | 8 |
| | | | | | | | | | 1 | 8 | 7 | 8 | 6 | 7 | 8 | 8 | 8 | 8 | 6 | 7 | 6 | 6 | 7 | 8 | 8 |
| 4 | 8 | 8 | 8 | 7 | 7 | 8 | 8 | 8 | 5 | 8 | 7 | 8 | 4 | 7 | 9 | 9 | 8 | 7 | 7 | 8 | 7 | 4 | 7 | 8 | 8 |
| | | | | | | | | | 1 | 5 | 3 | 8 | 1 | 3 | 8 | 6 | 8 | 6 | 3 | 6 | 0 | 0 | 7 | 6 | 8 |
| 5 | 8 | 7 | 8 | 8 | 5 | 8 | 8 | 8 | 5 | 6 | 4 | 8 | 6 | 7 | 8 | 7 | 8 | 7 | 7 | 8 | 7 | 7 | 8 | 8 | 8 |
| | | | | | | | | | 1 | 4 | 1 | 7 | 2 | 6 | 7 | 5 | 7 | 4 | 3 | 7 | 4 | 3 | 7 | 4 | 7 |
| 6 | 7 | 7 | 7 | 7 | 8 | 8 | 9 | 7 | 5 | 7 | 6 | 7 | 6 | 8 | 8 | 8 | 6 | 9 | 8 | 8 | 6 | 8 | 7 | 8 | 8 |
| | | | | | | | | | 1 | 6 | 4 | 6 | 5 | 7 | 7 | 7 | 5 | 6 | 7 | 8 | 3 | 7 | 7 | 8 | 8 |
| 7 | 7 | 8 | 8 | 7 | 4 | 8 | 8 | 7 | 5 | 6 | 7 | 8 | 7 | 7 | 8 | 8 | 8 | 7 | 9 | 8 | 7 | 7 | 7 | 8 | 8 |
| | | | | | | | | | 1 | 5 | 4 | 8 | 3 | 6 | 7 | 7 | 8 | 4 | 8 | 8 | 5 | 3 | 7 | 8 | 8 |
| 8 | 8 | 8 | 8 | 8 | 7 | 8 | 9 | 7 | 5 | 7 | 7 | 8 | 8 | 8 | 9 | 8 | 8 | 9 | 6 | 8 | 7 | 7 | 8 | 8 | 8 |
| | | | | | | | | | 1 | 6 | 7 | 8 | 7 | 7 | 8 | 8 | 8 | 8 | 6 | 8 | 6 | 7 | 7 | 8 | 8 |
| 9 | 6 | 7 | 8 | 7 | 7 | 8 | 9 | 7 | 5 | 6 | 6 | 8 | 6 | 8 | 8 | 9 | 7 | 7 | 6 | 8 | 6 | 8 | 6 | 9 | 8 |
| | | | | | | | | | 1 | 3 | 1 | 7 | 0 | 7 | 7 | 6 | 6 | 4 | 0 | 1 | 2 | 3 | 3 | 7 | 8 |
| 10 | 7 | 8 | 8 | 7 | 6 | 7 | 8 | 7 | 5 | 7 | 7 | 8 | 7 | 7 | 8 | 9 | 8 | 8 | 8 | 8 | 6 | 8 | 7 | 8 | 8 |
| | | | | | | | | | 1 | 5 | 6 | 8 | 5 | 7 | 8 | 7 | 8 | 4 | 6 | 5 | 3 | 4 | 6 | 7 | 8 |
| 11 | 7 | 6 | 7 | 6 | 5 | 7 | 8 | 5 | 5 | 7 | 6 | 7 | 6 | 7 | 8 | 7 | 7 | 8 | 8 | 8 | 4 | 5 | 6 | 7 | 8 |
| | | | | | | | | | 1 | 5 | 4 | 7 | 2 | 6 | 7 | 7 | 6 | 4 | 4 | 7 | 2 | 3 | 5 | 7 | 8 |
| 12 | 5 | 6 | 6 | 4 | 4 | 7 | 6 | 4 | 5 | 6 | 6 | 8 | 5 | 7 | 8 | 8 | 7 | 6 | 8 | 6 | 5 | 6 | 7 | 8 | 8 |
| | | | | | | | | | 1 | 3 | 2 | 6 | 3 | 5 | 8 | 6 | 6 | 3 | 2 | 3 | 2 | 2 | 6 | 4 | 7 |
| 13 | 4 | 3 | 7 | 4 | 2 | 7 | 4 | 4 | 5 | 4 | 0 | 7 | 5 | 5 | 7 | 6 | 6 | 4 | 4 | 5 | 3 | 2 | 4 | 2 | 3 |
| | | | | | | | | | 1 | 2 | 0 | 5 | 1 | 3 | 6 | 4 | 2 | 3 | 2 | 2 | 1 | 0 | 1 | 0 | 0 |
| 15 | 7 | 7 | 8 | 7 | 8 | 9 | 8 | 8 | 5 | 6 | 5 | 8 | 6 | 6 | 8 | 8 | 7 | 8 | 8 | 8 | 7 | 7 | 7 | 8 | 8 |
| | | | | | | | | | 1 | 6 | 2 | 7 | 4 | 6 | 8 | 7 | 7 | 7 | 4 | 8 | 6 | 3 | 7 | 8 | 8 |
| 16 | 8 | 7 | 8 | 7 | 7 | 9 | 8 | 8 | 5 | 6 | 3 | 5 | 3 | 6 | 6 | 6 | 4 | 6 | 3 | 7 | 6 | 3 | 6 | 7 | 2 |
| | | | | | | | | | 1 | 3 | 0 | 2 | 0 | 4 | 5 | 3 | 3 | 4 | 1 | 4 | 3 | 2 | 2 | 5 | 0 |
| 18 | 6 | 4 | 5 | 6 | 2 | 7 | 7 | 6 | 5 | 4 | 4 | 7 | 6 | 6 | 7 | 6 | 6 | 6 | 6 | 7 | 8 | 2 | 7 | 8 | 8 |
| | | | | | | | | | 1 | 2 | 0 | 2 | 3 | 1 | 5 | 4 | 2 | 4 | 2 | 4 | 4 | 0 | 1 | 4 | 2 |
| 19 | 7 | 7 | 7 | 7 | 7 | 7 | 8 | 7 | 5 | 6 | 4 | 7 | 6 | 7 | 8 | 7 | 6 | 8 | 8 | 8 | 7 | 7 | 7 | 8 | 8 |
| | | | | | | | | | 1 | 4 | 2 | 6 | 5 | 6 | 6 | 4 | 5 | 6 | 4 | 6 | 7 | 3 | 4 | 6 | 8 |
| 20 | 4 | 2 | 4 | 3 | 0 | 7 | 8 | 4 | 5 | 4 | 2 | 5 | 4 | 3 | 8 | 7 | 4 | 5 | 2 | 3 | 2 | 2 | 6 | 4 | 2 |
| | | | | | | | | | 1 | 1 | 0 | 1 | 2 | 0 | 6 | 2 | 2 | 2 | 0 | 0 | 0 | 0 | 0 | 0 | 0 |
| 21 | 8 | 8 | 8 | 8 | 7 | 8 | 9 | 8 | 5 | 8 | 7 | 7 | 7 | 8 | 8 | 9 | 8 | 8 | 9 | 9 | 8 | 8 | 7 | 8 | 8 |
| | | | | | | | | | 1 | 6 | 6 | 7 | 6 | 6 | 8 | 9 | 8 | 8 | 9 | 9 | 7 | 7 | 7 | 8 | 8 |
| 22 | 4 | 5 | 5 | 3 | 2 | 7 | 5 | 6 | 5 | 6 | 4 | 7 | 4 | 6 | 7 | 7 | 8 | 5 | 7 | 6 | 3 | 2 | 5 | 7 | 8 |
| | | | | | | | | | 1 | 4 | 2 | 6 | 1 | 4 | 6 | 5 | 7 | 3 | 4 | 4 | 1 | 0 | 5 | 6 | 8 |
| 23 | 7 | 7 | 8 | 7 | 6 | 7 | 7 | 7 | 5 | 7 | 6 | 7 | 7 | 7 | 8 | 8 | 8 | 8 | 7 | 8 | 7 | 6 | 7 | 7 | 8 |
| | | | | | | | | | 1 | 7 | 5 | 7 | 6 | 7 | 7 | 8 | 8 | 0 | 5 | 7 | 5 | 5 | 7 | 6 | 8 |
| 24 | 7 | 7 | 8 | 7 | 8 | 8 | 8 | 8 | 5 | 8 | 7 | 8 | 7 | 7 | 8 | 8 | 8 | 9 | 9 | 9 | 8 | 9 | 8 | 8 | 8 |
| | | | | | | | | | 1 | 7 | 6 | 7 | 6 | 7 | 8 | 7 | 8 | 8 | 8 | 8 | 7 | 8 | 8 | 8 | 8 |
| 25 | 8 | 7 | 7 | 8 | 7 | 8 | 8 | 8 | 5 | 8 | 7 | 8 | 7 | 8 | 8 | 8 | 8 | 9 | 8 | 8 | 8 | 8 | 8 | 8 | 8 |
| | | | | | | | | | 1 | 7 | 6 | 7 | 7 | 7 | 8 | 8 | 8 | 8 | 8 | 8 | 7 | 8 | 8 | 8 | 8 |
| 26 | 3 | 0 | 4 | 2 | 0 | 7 | 2 | 4 | 5 | 2 | 0 | 7 | 0 | 5 | 7 | 6 | 6 | 3 | 0 | 0 | 2 | 1 | 6 | 2 | 4 |
| | | | | | | | | | 1 | 0 | 0 | 0 | 0 | 2 | 7 | 2 | 4 | 1 | 0 | 0 | 0 | 0 | 5 | 0 | 3 |
| 27 | 8 | 8 | 8 | 8 | 8 | 8 | 9 | 8 | 5 | — | — | — | — | — | — | — | — | — | — | — | — | — | — | — | — |
| | | | | | | | | | 1 | 7 | 6 | 8 | 7 | 8 | 8 | 9 | 8 | 7 | 8 | 9 | 7 | 8 | 8 | 8 | 8 |
| 28 | 4 | 4 | 7 | 4 | 3 | 7 | 8 | 7 | 5 | 5 | 5 | 8 | 4 | 7 | 8 | 8 | 7 | 7 | 3 | 8 | 4 | 2 | 8 | 8 | 8 |
| | | | | | | | | | 1 | 1 | 2 | 5 | 1 | 4 | 8 | 6 | 6 | 2 | 0 | 2 | 1 | 1 | 4 | 2 | 2 |
| 29 | 6 | 5 | 6 | 4 | 3 | 7 | 7 | 7 | 5 | 7 | 6 | 8 | 6 | 2 | 8 | 7 | 8 | 8 | 7 | 7 | 7 | 2 | 8 | 8 | 8 |
| | | | | | | | | | 1 | 6 | 4 | 7 | 4 | 0 | 8 | 6 | 8 | 8 | 5 | 6 | 5 | 1 | 7 | 8 | 7 |

We claim:

1. A compound of the formula (I)

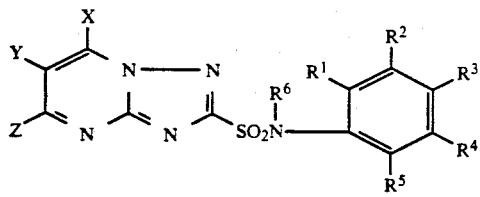

wherein Y is hydrogen; X and Z independently are $C_{1-4}$ alkyl; $R^2$, $R^3$, and $R^4$ are hydrogen; $R^1$ is —A(CH$_2$)$_n$—BR$^{10}$, —O(CH$_2$)$_n$O(CH$_2$)$_m$OR$^{10}$, or

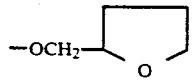

wherein A and B independently represent —O— or —S—, n and m are independently integers from 1 to 3, and $R^{10}$ is hydrogen, $C_{1-4}$ alkyl or phenyl; $R^5$ is hydrogen, fluorine, chlorine, nitro, $C_{1-4}$ alkoxy or —A(CH$_2$)$_n$—BR$^{10}$, and $R^6$ is hydrogen, alkanoyl of up to 4 carbon atoms, $C_{1-4}$ alkyl or the group:

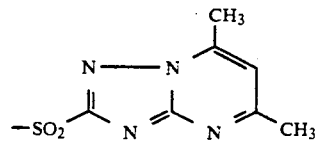

or a salt thereof.

2. A compound as claimed in claim 1, wherein $R^1$ is —O(CH$_2$)$_m$—OR$^{10}$, —O(CH$_2$)$_n$O(CH$_2$)$_m$OR$^{10}$ or

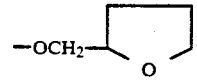

in which m and n are as defined in claim 1 and $R^{10}$ is hydrogen or $C_{1-4}$ alkyl.

3. A compound as claimed in claim 2, in which X and Y are both methyl, $R^1$ is —OCH$_2$CH$_2$OR$^{10}$ in which $R^{10}$ is $C_{1-4}$ alkyl, $R^5$ is chlorine or nitro, and $R^6$ is hydrogen or acetyl.

4. A compound as claimed in claim 3, wherein $R^6$ is hydrogen, and $R^1$ is —OCH$_2$CH$_2$OR$^{10}$ in which $R^{10}$ is methyl, ethyl, or propyl.

5. A herbicidal composition which comprises a carrier and, as an active ingredient, at least one compound of formula (I), or a salt thereof, as claimed in any one of claims 1, 2, 3 or 4.

6. A method of preventing or combating undesired plant growth at a locus which comprises treating said plant growth or locus with a compound of formula (I), or a salt thereof, as claimed in any one of claims 1, 2, 3 or 4.

7. A method of preventing or combating undesired plant growth at a locus which comprises treating said plant growth or locus with a herbicidal composition as claimed in claim 6.

* * * * *